US008628488B2

(12) United States Patent  
Serola

(10) Patent No.: US 8,628,488 B2  
(45) Date of Patent: Jan. 14, 2014

(54) COMPRESSION WRAP

(76) Inventor: Richard J. Serola, Roscoe, IL (US)

( * ) Notice: Subject to any disclaimer, the term of this patent is extended or adjusted under 35 U.S.C. 154(b) by 1070 days.

(21) Appl. No.: 11/552,875

(22) Filed: Oct. 25, 2006

(65) Prior Publication Data

US 2008/0188788 A1   Aug. 7, 2008

(51) Int. Cl.
*A41F 9/00* (2006.01)
*A41F 3/02* (2006.01)
*A61F 5/37* (2006.01)
*A61F 13/00* (2006.01)
*A61B 19/00* (2006.01)
*A61F 5/00* (2006.01)
*A61F 15/00* (2006.01)
*A61F 13/06* (2006.01)
*A61L 15/00* (2006.01)

(52) U.S. Cl.
USPC .............. 602/75; 2/311; 2/312; 2/313; 2/338; 128/846; 128/869; 128/876; 128/878; 602/12; 602/20; 602/21; 602/23; 602/60; 602/61; 602/62; 602/63

(58) Field of Classification Search
USPC ............. 602/2, 13–14, 20–21, 23, 26, 53, 75, 602/60–63; 607/108–111, 311–313, 321, 607/338; 2/16, 162, 170, 129, 338; 128/846, 869, 876, 878
See application file for complete search history.

(56) References Cited

U.S. PATENT DOCUMENTS

| | | |
|---|---|---|
| 2,957,475 A | 10/1960 | Drake |
| 3,586,001 A | 6/1971 | Sanderson |
| 3,970,081 A | 7/1976 | Applegate, Jr. |
| 4,243,028 A | 1/1981 | Puyana |
| 4,628,918 A | 12/1986 | Johnson, Jr. |
| 5,165,402 A | 11/1992 | McCoy |
| 5,295,951 A | 3/1994 | Fareed |
| 5,312,322 A | 5/1994 | Santana |
| 5,372,575 A | 12/1994 | Sebastian |
| 5,744,080 A * | 4/1998 | Kennedy et al. .............. 264/167 |
| 5,899,870 A * | 5/1999 | Deirmendjian et al. ........ 602/21 |
| 5,971,947 A | 10/1999 | McNally et al. |
| 6,149,617 A | 11/2000 | McNally et al. |
| 6,205,583 B1 | 3/2001 | Beland |
| 6,478,760 B2 | 11/2002 | Darcey |
| 6,755,800 B2 | 6/2004 | Weaver, II et al. |
| 7,211,004 B2 * | 5/2007 | DeMarco ...................... 473/201 |

(Continued)

FOREIGN PATENT DOCUMENTS

GB   2 294 881   5/1996

*Primary Examiner* — Patricia Bianco
*Assistant Examiner* — Brandon L Jackson
(74) *Attorney, Agent, or Firm* — Reinhart Boerner Van Deuren P.C.

(57) ABSTRACT

A compression wrap for providing pressure to an injured portion of a joint of a limb is provided. The compression wrap includes a pocket portion for receiving compression insert. The compression wrap further includes a strap connected to the pocket portion and adjustably securing the compression wrap to the limb. A buckle loop connected to the opposite side of the pocket portion as the strap adjustably receives the strap to adjust the size of the strap. Further, the strap portion and the pocket portion are configured such that when the compression wrap is attached to the limb of a person having an injury proximate the joint, the pocket portion is positionable to apply a load to the location of the injury while the strap portion is spaced away from the crease of the joint.

15 Claims, 7 Drawing Sheets

(56) References Cited

U.S. PATENT DOCUMENTS

| | | | |
|---|---|---|---|
| D546,953 S * | 7/2007 | Young | D24/190 |
| D548,350 S * | 8/2007 | Jordan et al. | D24/190 |
| 7,322,780 B2 * | 1/2008 | Hill | 410/97 |
| 7,451,531 B2 * | 11/2008 | Israel et al. | 24/442 |
| 7,661,178 B2 * | 2/2010 | Israel et al. | 24/442 |
| 2002/0169407 A1 | 11/2002 | Glinsboeckel | |
| 2004/0210178 A1 | 10/2004 | Weaver, II et al. | |
| 2006/0122547 A1 | 6/2006 | Stewart, III et al. | |

\* cited by examiner

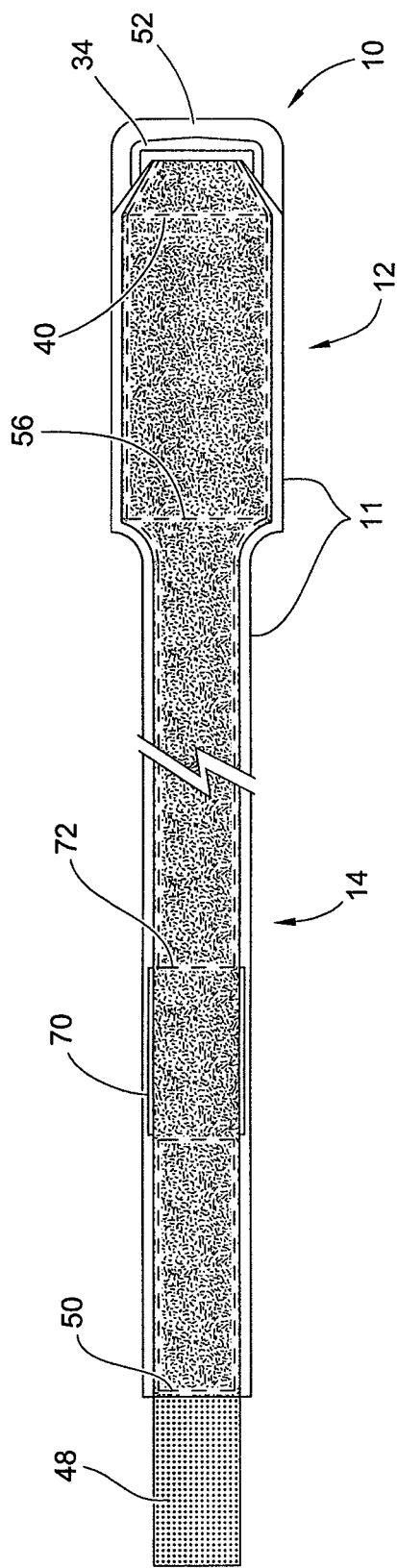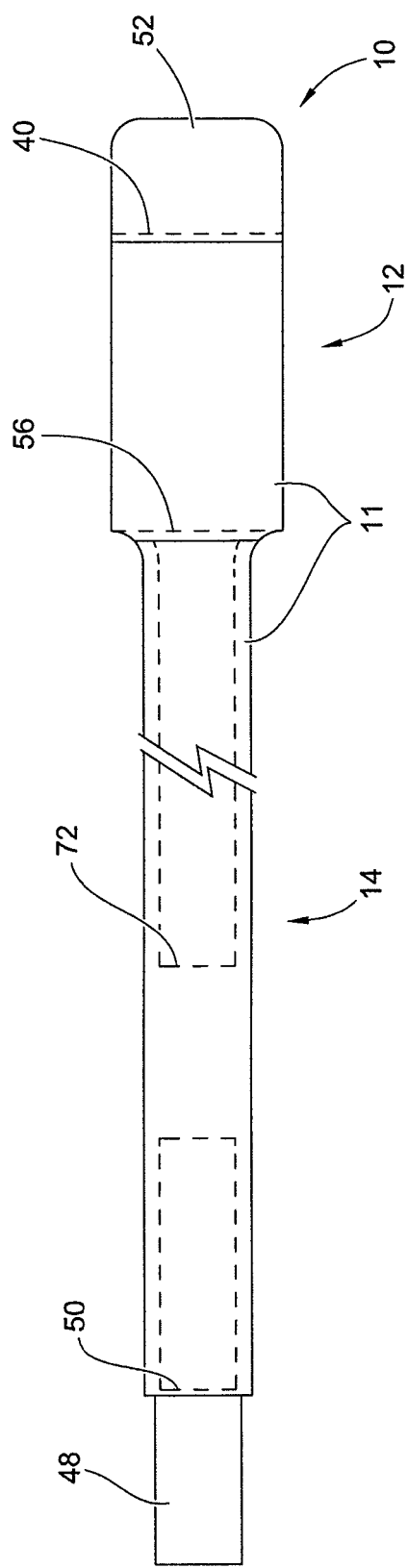

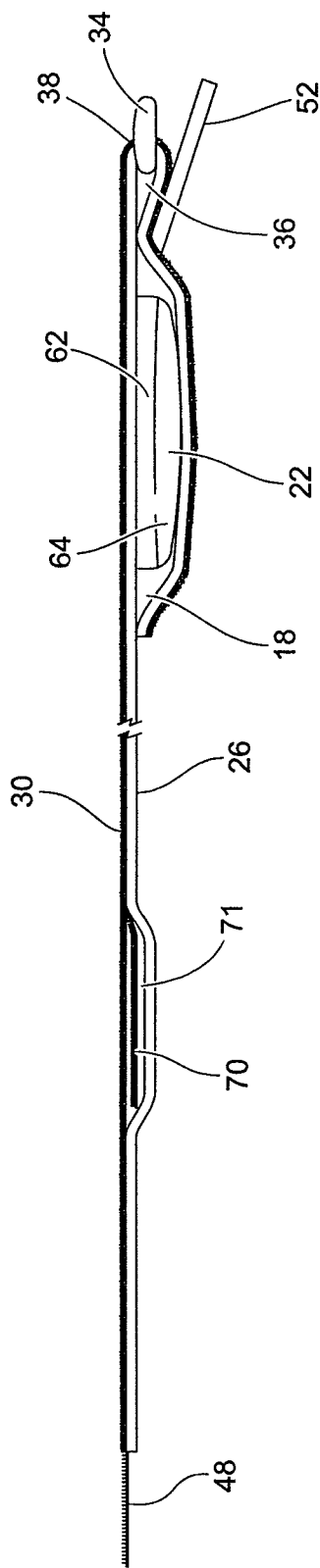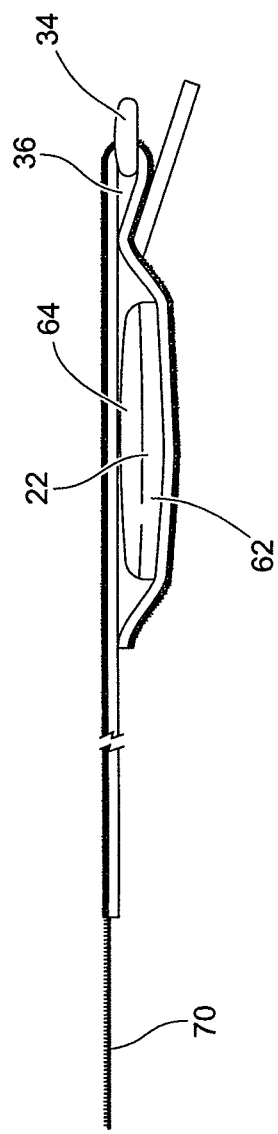
FIG. 7
FIG. 8

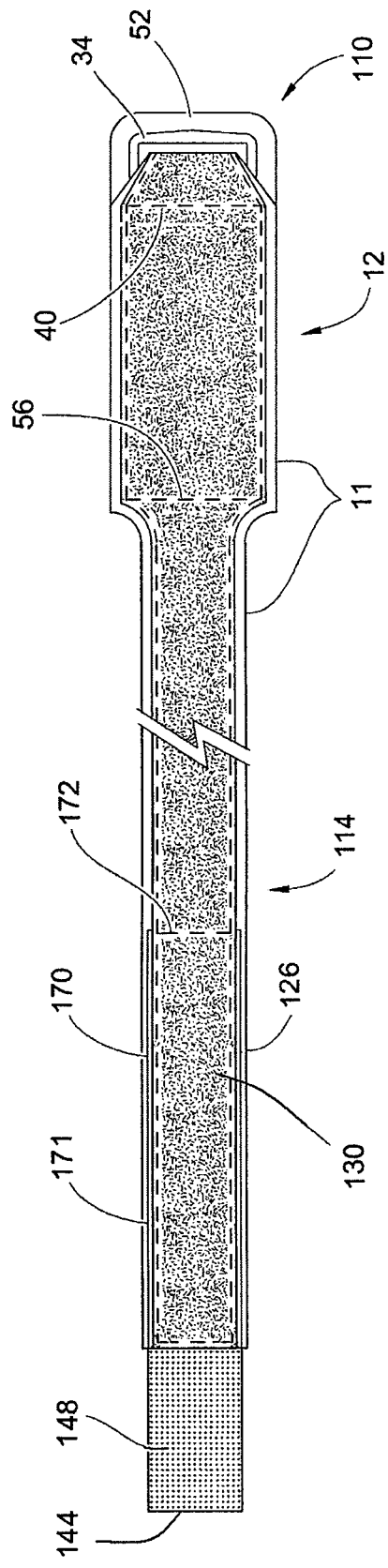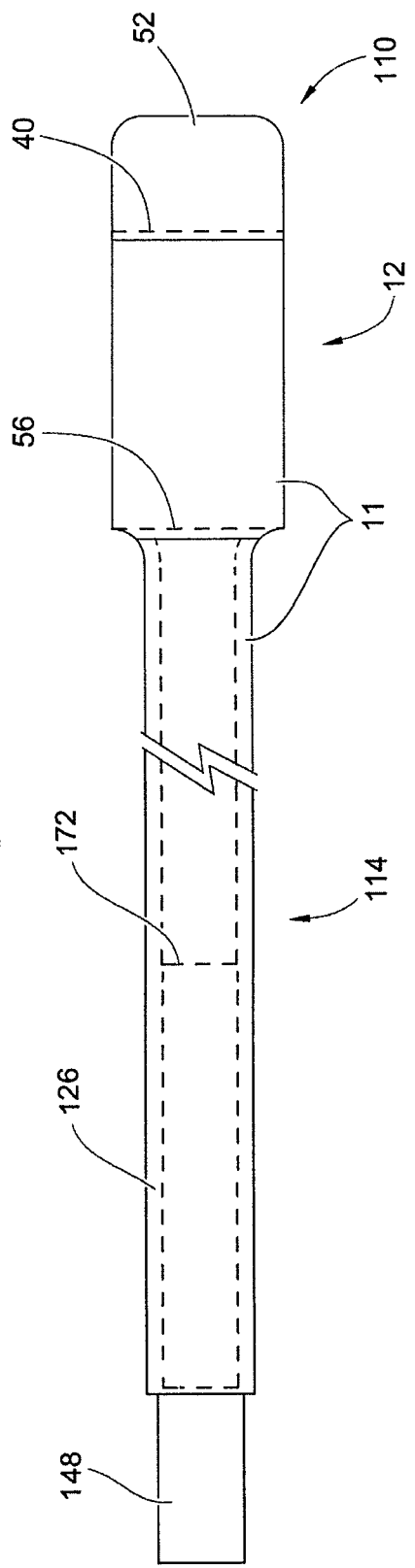
FIG. 11
FIG. 12

COMPRESSION WRAP

FIELD OF THE INVENTION

This invention generally relates to orthopedic devices, and more particularly to a wrap for applying a pressure to the upper forearm to relieve pain associated with lateral and medial epicondylitis.

BACKGROUND OF THE INVENTION

A common injury to people who play such sports as baseball or tennis, or to manual laborers such as construction workers is lateral epicondylitis, also known as, "tennis elbow." Tennis elbow is generally caused by overuse of the extensor tendons located proximate the elbow resulting in tears in the tendons at or near the lateral epicondyle. This is why such injury occurs from activities that require repeated flexure and movement of the elbow, e.g. when throwing a ball, swinging a racket or hammer, or twisting a screwdriver. Another common, related injury, is medial epicondylitis, also known as "Golfer's Elbow." Golfer's elbow is generally caused by overuse of the flexor tendons located just distal to the elbow and results in tears to the tendons near the medial epicondyle.

The best way to relieve the pain associated with and cure tennis elbow or golfer's elbow is to stop performing the activities that irritate the arm and allow the arm to heal. While this may be feasible for the weekend warrior athlete, this is not so easy for the manual laborer or professional athlete.

It has been found that pressure applied to the tendons prevents further irritation. The pressure is applied to healthy tissue of the tendon in a location as close to the injured tissue as possible without actually being applied to the injury. In effect, the pressure creates a secondary attachment point between the injury and the wrist flexor or wrist extensor that prevents the muscle from pulling on the injured area of the tendon. This generally relieves and/or eliminates the pain associated with tennis or golfer's elbow as well as facilitates recovery and healing of the irritated area.

Numerous devices have been designed to attempt to provide pressure or support to the injured area to reduce further injury or pain associated with tennis or golfer's elbow while facilitating continued use of the elbow. Some devices compress the muscle in an attempt to reduce the pull on the epicondyle. While such devices may be effective to relieve much of the pain associated with tennis elbow, they often restrict the contraction of the muscle, thereby limiting the usefulness of the muscle. Other devices are positioned closer to the epicondyle with the intention of placing pressure more on the tendons. These devices often irritate and chafe the user because the strap of the device often is positioned within the crease of the elbow in order to apply the pressure near the site of the pain. This irritation also affects or restricts the range of motion of the arm. Furthermore, many devices, although they are adjustable, either come in an adult size or a child size but are not sufficiently adjustable that only a single device can be sold that accommodates both an adult or a child.

There exists, therefore, a need in the art for an improved device for counteracting the effects of tennis and golfer's elbow.

BRIEF SUMMARY OF THE INVENTION

In one embodiment, an improved compression wrap for applying pressure to combat the effects of tennis elbow, golfer's elbow, or other injuries proximate joints is provided. The improved compression wrap is simple in design. Further, the improved compression wrap more effectively applies the requisite pressure to counteract the effects of tennis elbow. More particularly, the device includes a strap that encircles the arm without interfering with the crease of the elbow while including a pocket portion that holds an orthopedic device that applies the requisite pressure to the injury without restricting muscle function as prior devices do.

In another embodiment, a compression wrap provides multiple attachment strips such that the compression wrap can be adjusted from an adult size to a child size. Alternatively, an embodiment includes a single elongated attachment strip. In either embodiment, a portion of the compression wrap can be removed to shorten the length of the compression wrap. In particular, either at least one of the multiple attachment strips is removed or a portion of the elongated attachment strip is cut and removed when shortening the compression wrap.

In yet another embodiment, an improved compression wrap includes an elongated strap portion for adjustably securing the compression wrap proximate an injured joint of a limb of a wearer. A pocket portion is connected to a first end of the a strap portion and includes at least one side spaced outward from a corresponding side of the strap portion a substantial distance along an offset axis substantially orthogonal to the length of the strap portion. The pocket portion forms an insert pocket for receiving a compression insert. A buckle loop, sized to receive the strap portion therethrough, connects to the opposite side of the pocket portion as the strap portion and receives the strap portion therethrough.

In yet another embodiment an improved compression wrap generally includes a pocket portion and an elongated strap portion. A strap attachment is connected to the strap portion. The strap attachment includes first and second portions that releasably engage the strap portion. The first portion releasably engages the strap portion in a large configuration and the second portion releasably engages the strap portion in a small configuration. A buckle loop is connected proximate an opposite side of the pocket portion as the strap portion receives the strap portion therethrough. The plurality of attachment portions provide for easily adjusting the compression wrap from an adult size to a child size.

In another embodiment, the compression wrap is adjustable from the large size to the small size by removing a portion of the strap portion and the strap attachment.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings:

FIG. 3 is a top view illustration of the compression wrap of FIG. 1;

FIG. 4 is a bottom view illustration of the compression wrap of FIG. 1;

FIG. 7 is a side view illustration of the compression wrap of FIG. 1;

FIG. 8 is a side view illustration of the compression wrap of FIG. 1 having an end portion cut off to illustrate the adaptability of the compression wrap;

FIG. 11 is a top view of another embodiment of a compression wrap having a single attachment strip; and FIG. 12 is a bottom view of the embodiment of FIG. 11.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1:
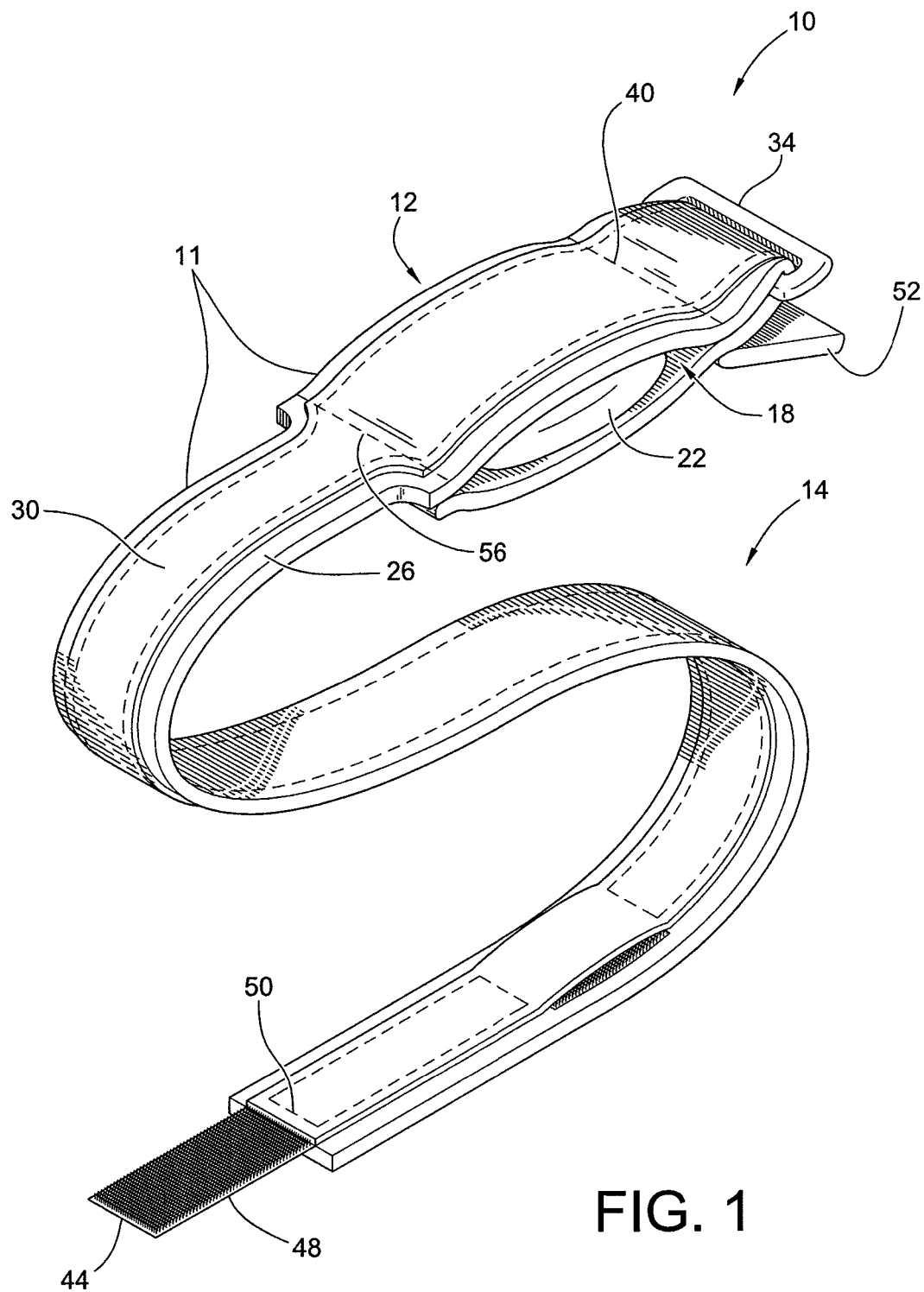
FIG. 1 is a perspective illustration of an compression wrap in accordance with one embodiment of the present invention.

Referring to the figures, FIG. 1 illustrates a compression wrap 10 according to one embodiment of the present invention. The compression wrap 10 generally includes a flexible body 11 that includes a pocket portion 12 and a strap portion 14. The pocket portion 12 defines a receiving pocket 18 that removably receives a compression wrap insert 22 for applying pressure to an injured portion of an elbow. The strap portion 14 allows for adjustably securing the compression wrap 10 to the arm of a wearer.

The body 11 is generally formed from an elongated strip of padding material 26 stitched to a strip of loop-type fastener material 30. In an embodiment, the elongated strip of padding material 26 is flexible and elastic. The padding material 26 may be made from and/or include neoprene or foam material. Further, the foam or neoprene material can be bonded to an elastic fabric backing. The flexible and elastic properties of the elongated strip of padding material 26 allow the body 11 to flex and bend to closely fit and conform to the contours of the elbow region of the wearer's arm.

The strip of loop-type fastener material 30, such as VELCRO, forms a second layer of material of the body 11. This strip of loop-type fastener material 30 is stitched to the elongated strip of padding material 26. The stitching is illustrated as dashed lines. In an embodiment, the strip of loop-type fastener material 30 is flexible but substantially inelastic. The inelasticity of the strip of loop-type fastener material 30 in that embodiment provides support for the elongated strip of padding material 26 and allows the compression wrap 10 to be tightened around and relative to the elbow region of the wearer while preventing substantial elongation of the elongated strip of padding material 26. The strip of loop-type fastener material 30 also function to provide releasable and adjustable securement of the compression wrap 10.

Figure 2:
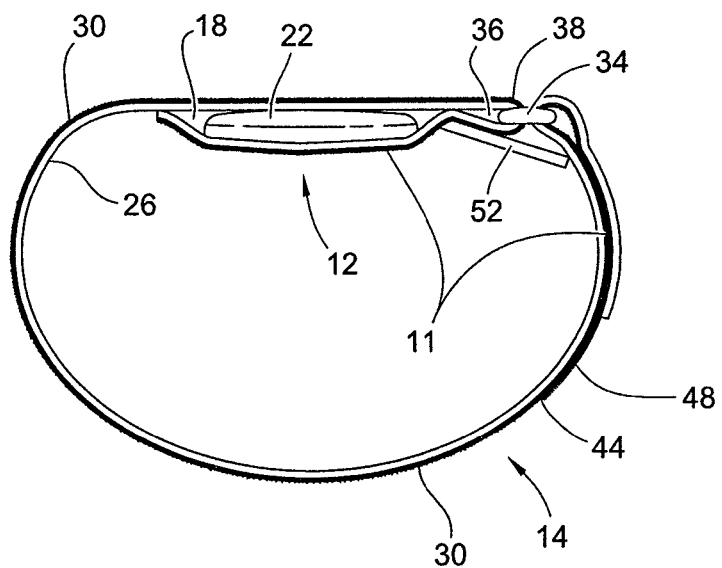
FIG. 2 is a side view illustration of the compression wrap of FIG. 5 having the compression wrap in a position as though it were mounted to an arm.

The compression wrap 10 further includes a buckle loop, e.g. in the form of D-ring 34 attached to the body 11 proximate the pocket portion 12. The D-ring 34 is generally rectangular in shape and is preferably formed from plastic. However, the D-ring 34 need not be generally rectangular and can be formed from other substantially rigid materials such as metal. As best illustrated in FIG. 2, a mounting pocket 36 formed proximate the pocket portion 12 receives and secures one side of the D-ring 34 therein to secure the D-ring 34 to the body 11. The mounting pocket 36 is formed by folding over a portion of the body 11 at fold 38 and stitching the two over lapping layers of the body 11 to one another at stitch 40 (see FIG. 1). In an embodiment, the portion of material that forms the mounting pocket 36 is tapered inward such that fold 38 and the D-ring 34 are narrower than the width of the pocket portion 12.

The D-ring 34 is sized to receive the strap portion 14 therethrough. As illustrated in FIG. 2, the D-ring 34 functions to allow the strap portion 14 to be folded back on itself. Particularly, the free end 44 of the strap portion 14 is fed through the aperture of the D-ring 34 and then fold back on itself and secured using an attachment strip 48 formed from a strip of hook-type fastener material, such as VELCRO, that is configured to releasably engage the loop-type fastener material 30. This configuration allows the size of the compression strap 10 to be easily adjusted by passing more or less of the strap portion 14 through the D-ring 34 and then back on itself to engage the loop-type fastener material 30 with the attachment strip 48.

As best illustrated in FIGS. 3 and 4, the attachment strip 48 defines a free end 44 of the compression wrap 10, opposite D-ring 34. The attachment strip 48 is stitched between the strip of loop-type fastener material 30 and the elongated strip of padding material 26 at stitch 50.

An arm guard 52 positioned proximate and below the D-ring 34 prevents contact between the wearer's arm and the D-ring 34 to protect the wearer's arm from irritation. The arm guard 52 can be formed from foam, neoprene or other padding materials. Preferably, the arm guard 52 is stitched to the body 11 with stitch 40 that forms the mounting pocket 36.

As identified previously, the pocket portion 12 of the compression wrap 10 forms the receiving pocket 18 for receiving the compression wrap insert 22. The receiving pocket 18 is formed between the overlapping layers of the body 11. More particularly, the overlapping layers of the body 11 are secured together at stitches 56 and stitch 40 forming the receiving pocket 18 therebetween. As illustrated in FIG. 2, the pocket extends inward toward the center of the loop formed by the compression wrap 10 when in a secured position.

As illustrated in FIGS. 1 and 2, the two layers of the body 11 that form the receiving pocket 18 are only stitched together at the ends of the receiving pocket 18 at stitches 40 and 56, but are not stitched at the sides of the receiving pocket 18 to provide access to the receiving pocket 18 for adjusting the position of the compression wrap insert 22 from either side of the compression wrap 10. As such, the compression wrap insert 22 may be removed from the compression wrap 10 and flipped over or rotated to adjust the pressure application of the compression wrap 10. This also allows the compression wrap to be applied to either the left or right arm of the wearer while orienting the arm guard 52 and the D-ring 34 in a similar position on either arm by simply rotating the compression wrap insert 22 180 degrees.

Figure 5:
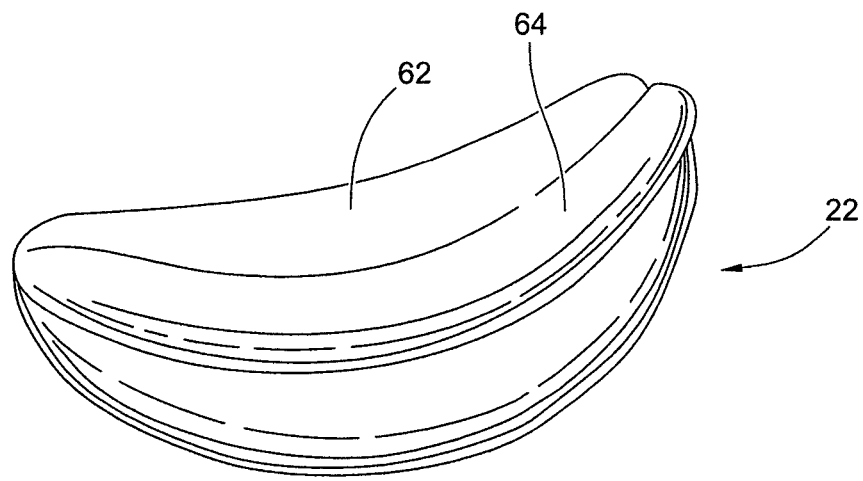
FIG. 5 is a top perspective illustration of the prosthetic insert of FIG. 1.
Figure 6:
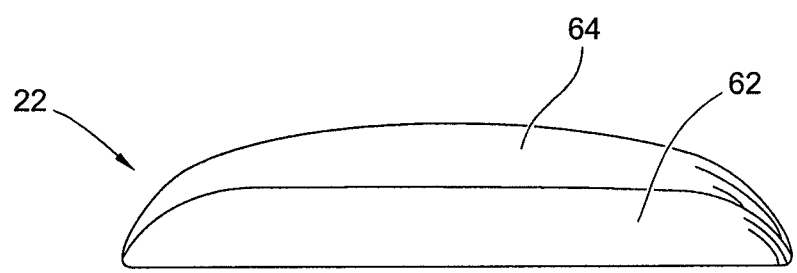
FIG. 6 is a front view of the prosthetic insert of FIG. 1.

With reference to FIGS. 5 and 6, the compression wrap insert 22 includes a base portion 62 and a raised portion 64 and is substantially moon shaped. In an embodiment, the compression wrap insert 22 is semi-compressible. In a further embodiment, the compression wrap insert 22 is formed from a silicone rubber or similar material. As illustrated in FIGS. 7 and 8, the compression wrap insert 22 can be positioned within the receiving pocket 18 with either the raised portion 64 downward and positioned toward the short folded over portion of the body 11 (see FIG. 7) or with the base portion 62 downward and positioned toward the short folded over portion of the body 11 (see FIG. 8). When it is preferred to have a more localized loading on the injured portion of the elbow, the compression wrap insert 22 is positioned as illustrated in FIG. 7. In this configuration, the raised portion 64 provides more of a point load to the wearer's elbow region. When it is preferred to provide less localized and more distributed pressure on the injured portion of the elbow, the compression wrap insert 22 is positioned as illustrated in FIG. 8. In this configuration, the larger surface area of the base portion 62 distributes the pressure more evenly.

As is illustrated in FIG. 7, the illustrated embodiment includes a second attachment strip 70. This second attachment strip 70 is positioned between the strip of loop-type fastener material 30 and the elongated strip of padding material 26 within pocket 71. Stitch 72 secures one end of the second attachment strip 70 between the other two layers of material. The other three sides of the second attachment strip 70 are free and unstitched. The second attachment strip 70 functions as an alternative attachment mechanism and allows the compression wrap 10 to be altered to fit smaller wearers such as from an adult size (large size) to a child size (small size). This configuration is highly beneficial because only a single size compression wrap need be manufactured and sold, but yet it can be initially configured to fit substantially any size wearer.

If the compression wrap 10 needs to be shortened for a smaller wearer, the wearer removes the unnecessary additional length of material beyond stitch 72. Specifically, the user would merely cut the strip of loop-type fastener material 30 as well as the elongated strip of padding material 26 within pocket 71. In doing so, the first attachment strip 48 and a portion of the strap portion 14 to which attachment strip 48 is secured are severed from the rest of the body 11 and removed. It is preferred that the user trim the strap portion 14 so that as much of the surface area of the second attachment strip 70 is exposed for securing the compression wrap 10 in a secured position. While the previous embodiment was described as having two attachment strips, more than two attachment strips may be incorporated.

In an alternative embodiment, the compression wrap 110 includes only a single long attachment strip 171 that includes an exposed portion 148 and a hidden portion 170 instead of the two separate attachment strips 48 and 70 of the previous embodiment. The long attachment strip 171 is secured at stitch 172 as well as the side stitches that run the length of the strap portion 114. The compression wrap 110 is shorted from a large configuration to a small configuration by cutting all the way through the strap portion 114, i.e. through the loop-type fastener material 130 and the elongated strip of padding material 126, and the long attachment strip 171. The cut is made somewhere between the free end of the strap portion 114 (i.e. the portion proximate to exposed portion 148) and stitch 172. After the excess length is removed, the layer of loop-type fastener material 130 could be removed or folded to expose the remaining portion of the long attachment strip 171. Preferably, between about ¾ inch and about 2 inches of the hidden portion 170 of the long attachment strip 171 remains after cutting the strap portion 114. After cutting, the long attachment strip 171 is primarily secured to the strap portion 114 via stitch 172.

In an embodiment, backtacking may be incorporated instead of the transverse stitching, i.e. stitches such as stitch 172. Backtacking occurs where a single stitch is passed over multiple times to lock the stitch. Furthermore, in an embodiment, the stitching that runs generally parallel with the length of the strap portion 114 may be backtacked proximate stitch 172 to prevent that stitching from coming undone when the excess portion of strap portion 114 is removed.

As illustrated in FIGS. 3 and 4 the width of the pocket portion 12 is wider than the width of the strap portion 14. The width of the pocket portion 12 can be sized such that each side of the pocket portion 12 extends approximately between about ⅛ inch to about ½ inch beyond the sides of the strap portion 14. As such the sides of the pocket portion 12 are positioned a substantial distance outward from the sides of the strap portion 14. More particularly, the sides of the pocket portion 12 are displaced outward from the sides of the strap portion 14 in a direction substantially perpendicular to the length of the compression wrap 10.

Figure 9:
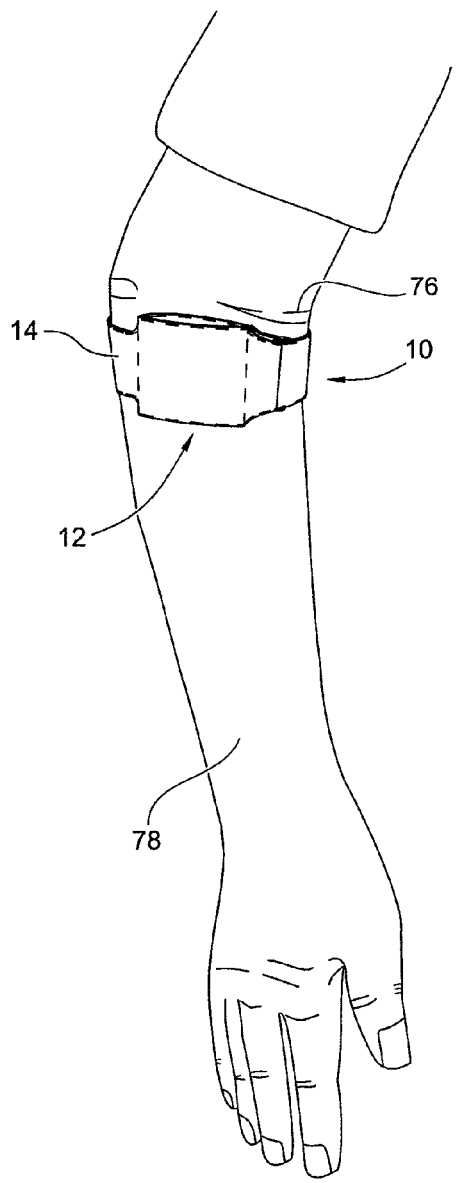
FIG. 9 is an illustration of the compression wrap of FIG. 1 mounted to an elbow, showing the exterior of the arm.
Figure 10:
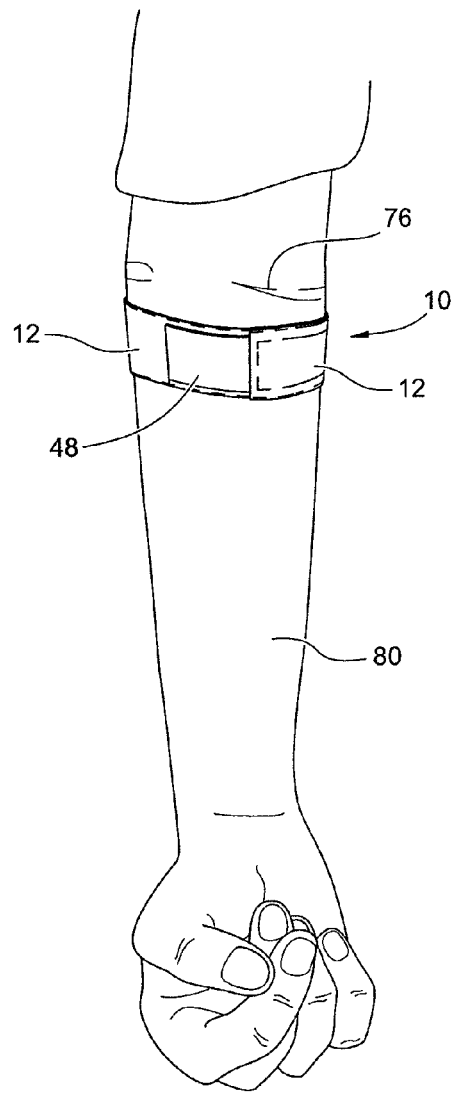
FIG. 10 is another illustration of the compression wrap of FIG. 1 mounted to an elbow showing the interior of the arm

With further reference to FIGS. 9 and 10, when attached to the wearer's arm, the pocket portion 12 is positioned proximate the outside 78 of the elbow region of the arm while the strap portion 14 is positioned proximate the inside 80 of the elbow region. The configuration of the compression wrap 10, i.e. having the pocket portion 12 substantially wider than the strap portion 14, is highly beneficial because the compression wrap insert 22 within the receiving pocket 22 can be more easily and more closely positioned relative to the injury of the tendons, i.e. over the tendons and not substantially on or restricting the forearm muscles, without requiring the strap portion 14 to be positioned within the crease 76 of the elbow region of the wearer. By not interfering with the crease 76 of the elbow, the compression wrap 10 does not restrict movement of the elbow or cause irritation of the elbow by repeatedly rubbing against the skin of the crease of the elbow.

While the illustrated embodiment provides this feature of allowing the pocket portion 12 to be positioned proximate the injury while preventing the strap portion 14 from interfering with the crease 76 of the elbow region by having both sides of the pocket portion 12 offset from the sides of the strap portion 12, the pocket portion could be otherwise configured to generate this effect. For example, only one side of the pocket portion 14 could be offset from the side of the strap portion 12 or the strap portion 14 and pocket portion 12 could be substantially uniform in width but the pocket portion could be offset from the strap portion. However, such configurations would limit the ability to apply the same compression wrap 10 to either arm.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compression wrap comprising:
a strap portion for adjustably securing the compression wrap proximate an injured joint of a limb of a user;
a pocket portion connected to a first end of the strap portion, the pocket portion having at least one side spaced outward from a corresponding side of the strap portion a substantial distance along an offset axis substantially orthogonal to the length of the strap portion, the pocket portion forming an insert pocket for receiving a compression insert;
wherein the compression insert receivable in the pocket portion, the compression insert including a base portion and a projection portion extending from the base portion, the base portion having a larger width than the projection portion;
a buckle loop, sized to receive the strap portion therethrough, connected to the opposite side of the pocket portion as the strap portion, the pocket portion being generally interposed between the strap portion and the buckle loop; and
wherein the width of the strap portion and the width of the pocket portion are configured such that when the compression wrap is attached proximate the injury of the joint, the pocket portion is positioned such that the pocket portion applies a loading proximate the injury while the strap portion is spaced away from a crease of the joint.

2. The compression wrap of claim 1, wherein the width of the pocket portion is between about ¼ inch and 1 inch wider than the strap portion along the offset axis.

3. The compression wrap of claim 2, wherein the strap portion is centered relative to the pocket portion such that between about ⅛ inch and about ½ inch of the pocket extends beyond each side of the strap portion along the offset axis.

4. The compression wrap of claim 1, wherein the pocket portion and strap portion are formed in a continuous unitary piece of material.

5. The compression wrap of claim 4, further comprising a piece of loop-type material attached to an outer surface of the unitary piece of material and the unitary piece of material being formed from a padding material and further comprising a strip of hook-type material releasably engageable with the loop-type material and attached proximate an end of the strap portion opposite the end proximate the pocket portion.

6. The compression wrap of claim 4, wherein the pocket portion and a mounting pocket securing the buckle loop are formed by an end portion of the unitary piece of material folded over onto itself and then connected thereto, the mounting pocket being formed between the fold and a connection connecting the folded over portion to the rest of the unitary piece of material and the insert pocket being formed between the first connection and a second connection connecting the folded over portion to the rest of the unitary piece of material, the second connection being proximate a terminating end of the unitary piece of material.

7. The compression wrap of claim 1, wherein the projection portion is a rib having a generally arcuate outer surface and the side of the base portion opposite the projection portion is generally flat.

8. The compression wrap of claim 1, wherein the joint is the elbow and the injury is lateral or medial epicondylitis.

9. A compression wrap comprising;
a pocket portion;
an elongated strap portion extending between an end connected to the pocket portion and an attachment end;
a strap attachment releasably engageable with the elongated strap portion to adjustably secure the compression wrap in a mounted condition, the strap attachment having a first portion that releasably engages the elongated strap portion when the compression wrap is in a large configuration and a second portion that is hidden in the large configuration and that is exposed and releasably engages the elongated strap portion when the compression wrap is in a small configuration; and
a buckle loop connected proximate an opposite side of the pocket portion as the strap portion, the buckle loop sized to receive the strap portion therethrough.

10. The compression wrap of claim 9, wherein the strap portion includes a loop-type material attached to a padding material and the strap attachment includes a hook-type material configured to releasably mate with the loop-type material, wherein in the large configuration the second portion is interposed between the padding material and the loop-type material such that hooks of the hook-type material are generally unexposed and in the small configuration hooks of the second portion are exposed.

11. The compression wrap of claim 10, wherein the compression wrap is adjustable by cutting at least the loop-type material and the padding material to expose hooks of the second portion.

12. The compression wrap of claim 11, wherein the compression wrap is adjustable by further cutting the strap attachment between the first portion and the second portion to remove the first portion.

13. The compression wrap of claim 9, wherein the strap attachment is a single unitary strip of material, wherein in the large configuration the second portion is hidden by the strap portion such that it is substantially prevented from engaging the elongated strap portion and in the small configuration the second portion is exposed such that it is permitted to engage the elongated strap portion.

14. The compression wrap of claim 13, wherein the compression wrap is adjustable from a large configuration to a small configuration by removing the first portion from the strap attachment and a portion of the strap portion extending from a connection securing the second portion of the strap attachment to the strap portion to and including the attachment end.

15. The compression wrap of claim 9, wherein the strap attachment includes at least two attachment strips, the first portion of the strap attachment includes a first attachment strip connected proximate to the attachment end and the second portion of the strap attachment includes a separate second attachment strip connected to the strap portion and interposed between the first attachment strip and the pocket portion.

* * * * *